(12) United States Patent
Ulger et al.

(10) Patent No.: US 8,905,052 B2
(45) Date of Patent: Dec. 9, 2014

(54) DISHWASHER

(75) Inventors: Zehra Ulger, Istanbul (TR); Erman Tutkak, Istanbul (TR); Emine Birci, Istanbul (TR); Meryem Guneri, Istanbul (TR); Ozlem Kaya, Istanbul (TR)

(73) Assignee: Arcelik Anonim Sirketi, Istanbul (TR)

( * ) Notice: Subject to any disclaimer, the term of this patent is extended or adjusted under 35 U.S.C. 154(b) by 1334 days.

(21) Appl. No.: 12/673,706

(22) PCT Filed: Aug. 13, 2008
(Under 37 CFR 1.47)

(86) PCT No.: PCT/EP2008/060638
§ 371 (c)(1),
(2), (4) Date: Dec. 20, 2010

(87) PCT Pub. No.: WO2009/021973
PCT Pub. Date: Feb. 19, 2009

(65) Prior Publication Data
US 2011/0226292 A1    Sep. 22, 2011

(30) Foreign Application Priority Data
Aug. 16, 2007   (TR) ................ a 2007 05702

(51) Int. Cl.
*A47L 15/42*    (2006.01)
*A47L 15/00*    (2006.01)

(52) U.S. Cl.
CPC ........... *A47L 15/424* (2013.01); *A47L 15/0015* (2013.01); *A47L 15/0007* (2013.01); *A47L 2601/08* (2013.01)
USPC ....... 134/198; 134/56 D; 134/57 D; 134/58 D

(58) Field of Classification Search
USPC ......................... 134/56 D, 57 D, 58 D, 198
See application file for complete search history.

(56) References Cited

U.S. PATENT DOCUMENTS

2006/0107976 A1 *   5/2006   Boyers et al. ................ 134/94.1
2007/0251549 A1 *  11/2007   Heiligenmann et al. ........ 134/31

FOREIGN PATENT DOCUMENTS

| WO | WO 2005039377 A1 * | 5/2005 |
| WO | WO 2006061281 A1 * | 6/2006 |
| WO | WO 2007110434 A1 * | 10/2007 |

* cited by examiner

*Primary Examiner* — Michael Barr
*Assistant Examiner* — Benjamin L Osterhout
(74) *Attorney, Agent, or Firm* — Venjuris PC

(57) ABSTRACT

The present invention relates to a dishwasher (1) wherein an ozone generator (8) that generates ozone is used for increasing the washing performance and to provide hygiene. The ozone gas generated by the ozone generator (8) is delivered directly on the objects in the tub (2) by means of an ozone supply line (9) without mixing with the wash water.

6 Claims, 3 Drawing Sheets

DISHWASHER

Figure 1:
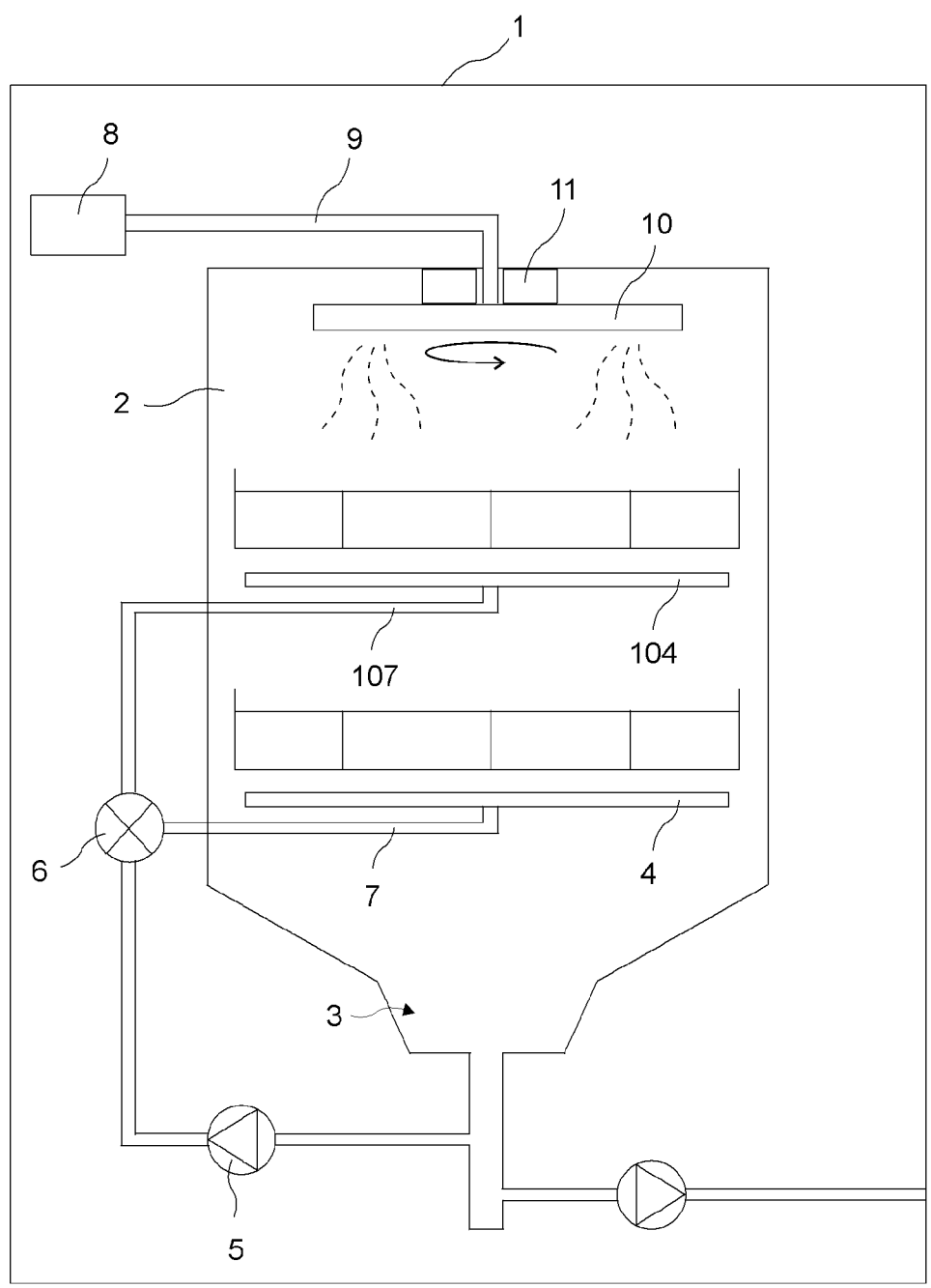

The present invention relates to a dishwasher wherein ozone gas is used in the washing process.

In dishwashers, ozone gas ($O_3$) having disinfectant and soil removing properties is used for increasing the effectiveness of the washing process. By means of the ozone gas used in the washing process, detergent and water consumption is reduced and energy savings is provided since the washing process can be performed at lower temperatures. The ozone gas generated by an ion generator is generally dissolved in the wash water and the washing process is performed by delivering ozone-water on the dishes. When the ozone gas is delivered into the wash water, the movement of the water causes ozone to be broken down into oxygen at least partially and the effectiveness of ozone decreases. A high capacity ozone generator has to be used for mixing ozone into water and costs increase. Moreover, when a vacuum pump is used for delivering ozone gas to water, the pressure for the rotation of the spray arm and the circulation pump required for absorption of ozone gas into water has to be more than normal and this is also a factor that increases costs. In order to effectively utilize ozone gas, there are implementations wherein ozone is directly delivered into the wash milieu without mixing with water, however in this case problems arise in ozone gas reaching to the dishes efficiently.

In the Patent Document No JP11128324, a dish housing device is explained that is used in crowded places like schools, wherein the dishes are dried after washing and disinfected by ozone gas. In this device the dishes are dried by a heater-motor-fan apparatus after being washed and disinfected by ozone gas afterwards. The ozone gas produced by an ozone generator is delivered into the housing container containing the dishes by means of a pipe.

In the Patent Document No DE3232057, an ozone generator is cited which is used in washing machines and dishwashers. In the dishwasher, the ozone gas delivered from the ozone generator to the washing line by a vacuum pump in the rinsing step is dissolved in the wash water and the dishes are washed by ozone-water.

In the Patent Application No EP1701644, the use of oxygenating gases like ozone in a dishwasher for purposes of cleaning and disinfecting is explained. The ozone gas is dissolved in the rinsing liquor and/or delivered directly to the washing container. Moreover, the effectiveness of ozone gas is increased by mixing with fog produced by an ultrasonic generator.

The object of the present invention is the realization of a dishwasher wherein the effectiveness of ozone gas used in washing is increased.

The dishwasher realized in order to attain the aim of the present invention is explicated in the claims.

In the dishwasher of the present invention, an ozone generator that generates ozone gas is used in order to provide hygiene of the washed objects and the ozone gas is directly applied on the washed objects without mixing with water in the sump and in the lines supplying water to the spray arms. In the dishwasher, furthermore an ozone spray arm is provided, connected to the end of the ozone supply line opening into the tub, maintaining to accelerate the ozone gas with the effect of centrifugal force produced by the rotational movement thereof to be delivered by spread on the objects washed in the tub.

The ozone spray arm is attached to the ceiling of the tub similar to the top spray arm in conventional dishwashers that spray the wash water and is rotated by an electric motor.

In the dishwasher a washing program comprised of pre-wash, main wash (washing with detergent) and cold-hot rinsing steps is implemented and ozone gas is delivered by spread into the tub by means of the ozone spray arm in at least one of the said washing steps.

In an embodiment of the present invention, the steam generated by a steam generator is mixed with the ozone gas and conveyed into the tub by the ozone spray arm, maintaining to deliver ozone gas effectively on the washed dishes.

The dishwasher realized in order to attain the aim of the present invention is illustrated in the attached figures, where:

FIG. 1—is the schematic view of a dishwasher comprising an ozone generator.

Figure 2:
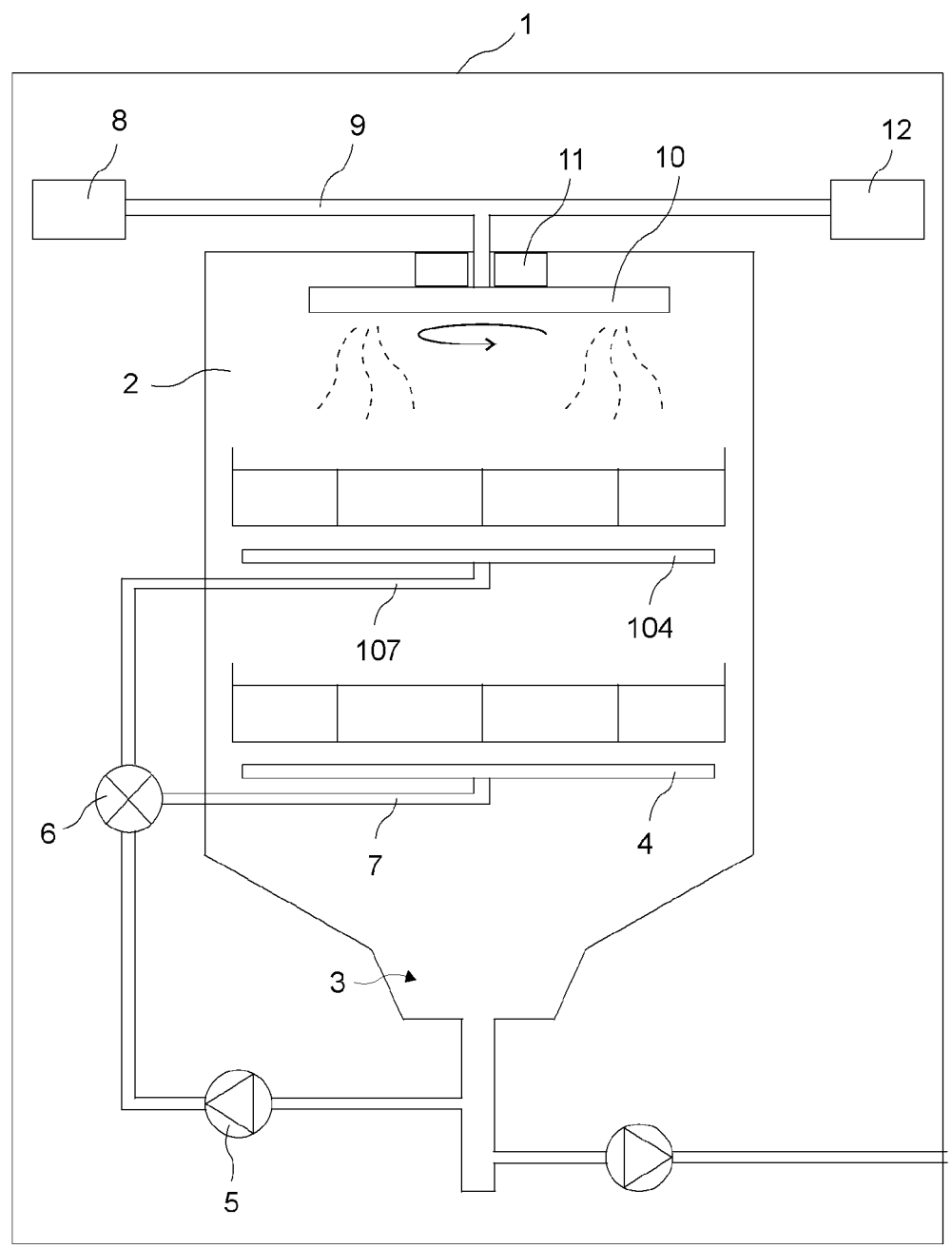

FIG. 2—is the schematic view of a dishwasher comprising an ozone generator and a steam generator.

Figure 3:
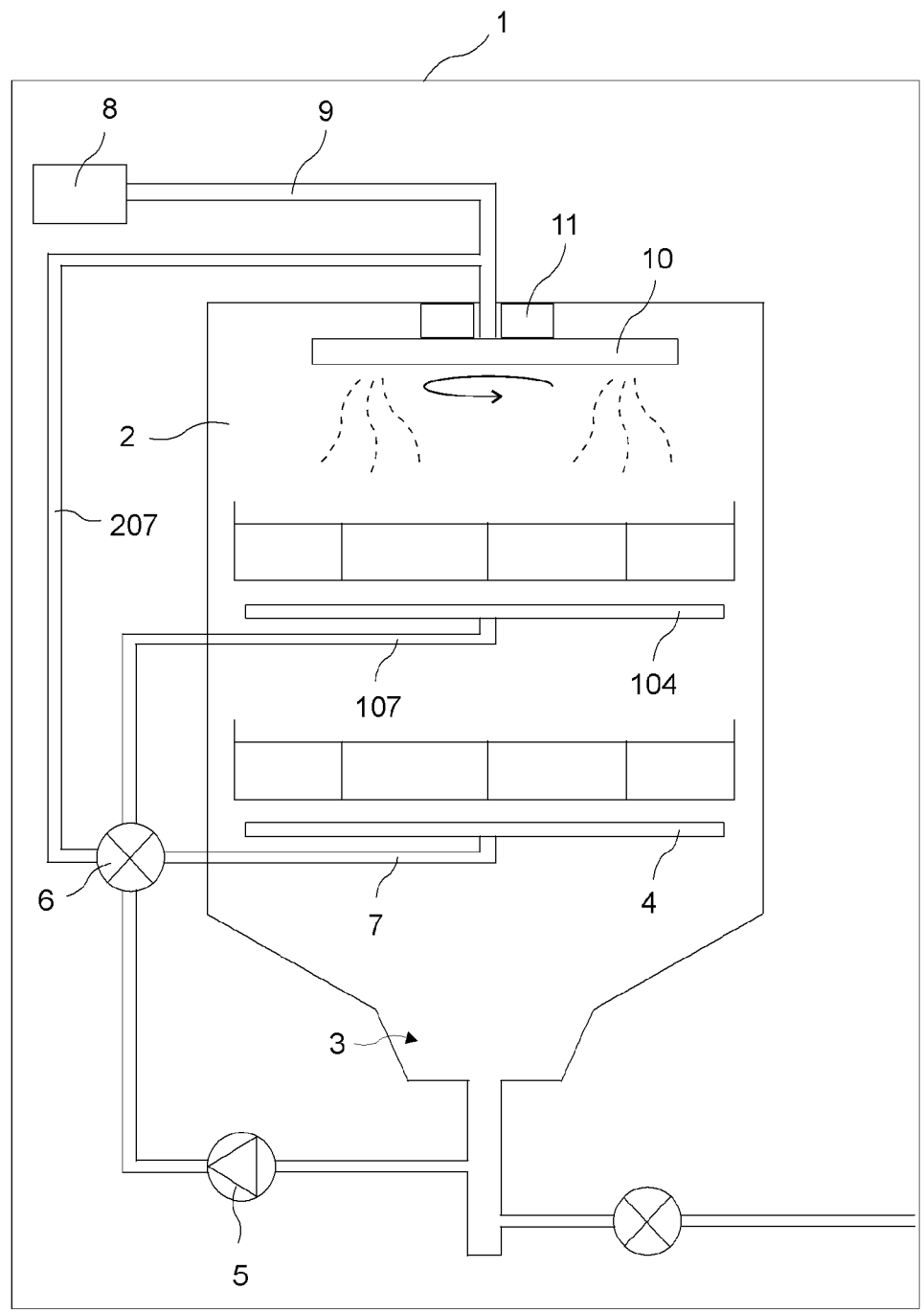

FIG. 3—is the schematic view of a dishwasher according to another embodiment of the present invention.

The elements illustrated in the figures are numbered as follows:
1. Dishwasher
2. Tub
3. Sump
4. 104 Spray arm
5. Circulation pump
6. Multi-way valve
7. 107, 207 Water supply line
8. Ozone generator
9. Ozone supply line
10. Ozone spray arm
11. Motor
12. Steam generator The dishwasher (1) comprises a tub (2) wherein the washing process is performed, a sump (3) wherein the water in the tub (2) is collected during the washing process, at least one basket for arranging orderly the objects to be washed in the tub (2), at least one spray arm (4, 104) for spraying the wash water on the objects arranged in the baskets, a circulation pump (5) for the circulation of the wash water, a multi-way valve (6) situated at the outlet of the circulation pump (5) for delivering water to the intended spray arm (4, 104) and at least one water supply line (7, 107) for conveying water from the multi-way valve (6) to the spray arms (4, 104).

The dishwasher (1) furthermore comprises an ozone generator (8) that produces ozone gas and an ozone supply line (9), with one end connected to the ozone generator (8) and the other end opening into the tub (2) for delivering ozone gas without mixing with the wash water in the sump (3) or the water supply line (7, 107).

The dishwasher (1) of the present invention furthermore comprises an ozone spray arm (10) connected to the end of the ozone supply line (9) opening into the tub (2) and maintaining to deliver the ozone gas by dispersing on the objects in the tub (2) with the effect of centrifugal force produced by the rotational movement thereof and a motor (11) for rotating the ozone spray arm (10) (FIG. 1-3).

The ozone spray arm (10) is attached to the ceiling of the tub (2) and provides the ozone gas to move from the top downwards for scanning the inner volume of the tub (2).

In the dishwasher (1) of the present invention, the ozone gas generated by the ozone generator (8) is delivered directly into the tub (2) by the ozone supply line (9), without mixing with the wash water in the sump (3) or passing through the water supply line (7, 107) and reaches the ozone spray arm (10) attached to the ceiling of the tub (2). Since the pressure of the ozone gas generated by the ozone generator (8) is not sufficient to rotate the ozone spray arm (10), the ozone spray arm (10) is rotated by a motor (11). The ozone spray arm (10)

sprays out the ozone gas contained therein from the spray nozzles by the effect of the rotational speed (for example 60 rpm) and the ozone gas is dispersed quickly into the tub (2) acting on the washed objects. The effectiveness of the ozone gas is increased by accelerating the rotational speed of the motor (11).

In the dishwasher (1), a washing program is implemented that is comprised of pre-wash, main wash (washing with detergent) and cold-hot rinsing steps and in at least one of the said washing steps ozone gas is delivered into the tub (2) by means of the ozone spray arm (10) for a predetermined period of time (e.g. for 10 minutes).

In another embodiment of the present invention, ozone gas delivery from the ozone supply line (9) is interrupted and the ozone spray arm (10) is halted, discontinuing the ozone gas application so that the chemical structure of the detergent used in washing does not deteriorate.

In another embodiment of the present invention, the dishwasher (1) comprises a steam generator (12) that is connected to the ozone supply line (9) for mixing water vapor with the ozone gas and to deliver the ozone-steam mixture into the tub (2) by means of the ozone spray arm (10). In this embodiment, water vapor serves the function of carrying ozone gas and for delivering ozone gas effectively on the washed objects (FIG. 2).

In another embodiment of the present invention, the dishwasher (1) comprises a water supply line (207) connected between the multi-way valve (6) and the ozone supply line (9) for delivering the wash water to the ozone spray arm (10) when desired. In this embodiment, when the ozone spray arm (10) does not deliver ozone gas or ozone-steam mixture, the ozone spray arm (10) operates like other spray arms (4, 104) that provide to wash with water and the motor (11) is deactivated. When ozone gas or ozone-steam mixture is to be applied, water delivery to the ozone spray arm (10) is interrupted from the multi-way valve (6) and the water supply line (207) and ozone gas is delivered from the water supply line (207) to the ozone spray arm (10) and the motor (11) is activated (FIG. 3).

In the ozone gas application by the ozone spray arm (10) of the present invention, the desired washing effectiveness and hygiene is maintained, and washing can be performed at low temperatures thereby providing savings in energy.

The invention claimed is:

1. A dishwasher (1) comprising a tub (2) wherein the washing process is performed, a sump (3) wherein the water in the tub (2) is collected during the washing process, at least one spray arm (4, 104) for spraying the wash water on the objects arranged in the baskets, at least one water supply line (7, 107) for delivering the wash water to the spray arms (4, 104), an ozone generator (8) that generates ozone gas and an ozone supply line (9), with one end connected to the ozone generator (8) and the other end connected to the tub (2) and an ozone spray arm (10) connected to the end of the ozone supply line (9) opening into the tub (2) and maintaining to deliver the ozone gas by dispersing on the objects in the tub (2) and a dedicated motor (11) only used for rotating the ozone spray arm (10); wherein the ozone gas is directly applied on the washed objects without mixing with water in the sump and in the lines supplying water to the spray arms.

2. The dishwasher (1) as in claim 1, wherein the ozone spray arm (10) that is attached to the ceiling of the tub (2).

3. The dishwasher (1) as in claim 1 or 2, wherein a washing program is implemented comprising pre-wash, main wash (washing with detergent) and cold-hot rinsing steps and characterized by the ozone spray arm (10) that delivers ozone gas into the tub (2) in at least one of the said washing steps for a predetermined period of time.

4. The dishwasher (1) as in claim 3, wherein the ozone spray arm (10) that is halted by interrupting ozone gas delivery during washing with detergent.

5. The dishwasher (1) as in claim 1 or 2, further comprising a steam generator (12) that generates steam, connected to the ozone supply line (9) for mixing water vapor with the ozone gas and to deliver the ozone-steam mixture into the tub (2) by means of the ozone spray arm (10).

6. The dishwasher (1) as in claim 1 or 2, further comprising a circulation pump (5) for the circulation of the wash water, a multi-way valve (6) situated at the outlet of the circulation pump (5) for delivering water to the desired spray arm (4, 104) and a water supply line (207) connected between the multi-way valve (6) and the ozone supply line (9) for delivering the wash water to the ozone spray arm (10) when desired.

* * * * *